(12) United States Patent
Hosokawa et al.

(10) Patent No.: US 10,961,958 B2
(45) Date of Patent: Mar. 30, 2021

(54) HUMIDITY DETECTION DEVICE

(71) Applicant: Hitachi Automotive Systems, Ltd., Hitachinaka (JP)

(72) Inventors: Takeo Hosokawa, Hitachinaka (JP); Hiroaki Hoshika, Hitachinaka (JP); Takayuki Yogo, Hitachinaka (JP); Takahiro Miki, Hitachinaka (JP); Yuki Isoya, Hitachinaka (JP)

(73) Assignee: Hitachi Automotive Systems, Ltd., Hitachinaka (JP)

(*) Notice: Subject to any disclaimer, the term of this patent is extended or adjusted under 35 U.S.C. 154(b) by 159 days.

(21) Appl. No.: 15/301,493

(22) PCT Filed: Mar. 25, 2015

(86) PCT No.: PCT/JP2015/059022
§ 371 (c)(1),
(2) Date: Oct. 3, 2016

(87) PCT Pub. No.: WO2015/151947
PCT Pub. Date: Oct. 8, 2015

(65) Prior Publication Data
US 2017/0037819 A1    Feb. 9, 2017

(30) Foreign Application Priority Data

Apr. 4, 2014 (JP) .............................. JP2014-077434

(51) Int. Cl.
*G01N 33/00* (2006.01)
*F02M 35/10* (2006.01)
(Continued)

(52) U.S. Cl.
CPC ... *F02M 35/10393* (2013.01); *F02D 41/1494* (2013.01); *F02D 41/26* (2013.01);
(Continued)

(58) Field of Classification Search
CPC ....... F02M 35/10393; F02M 35/10268; G01N 25/62; G01N 33/0016; F02D 41/26;
(Continued)

(56) References Cited

U.S. PATENT DOCUMENTS 5,005,410 A    4/1991   Webster et al.
6,126,311 A *  10/2000  Schuh ................... G01N 5/025
                                                    374/118
(Continued)

FOREIGN PATENT DOCUMENTS

CN    101650204 A    2/2010
JP    1-182746       7/1989
(Continued)

OTHER PUBLICATIONS

International Search Report (PCT/ISA/210) issued in PCT Application No. PCT/JP2015/059022 dated Jun. 30, 2015 with English translation (Two (2) pages).

(Continued)

*Primary Examiner* — Xin Y Zhong
(74) *Attorney, Agent, or Firm* — Crowell & Moring LLP

(57) ABSTRACT

The purpose of the present invention is to reduce a load of preventing dew condensation, and to provide a highly reliable humidity detection device. In order to achieve the purpose, this humidity detection device is provided with: a humidity sensor having a humidity detection unit and a temperature detection unit; a heating resistor that heats the humidity sensor; and a heating control unit that controls a heating temperature of the heating resistor. The humidity detection device is characterized in having a target temperature storage unit that stores target temperatures of the heating resistor, said target temperatures having been determined corresponding to temperatures and humidities.

11 Claims, 4 Drawing Sheets

(51) Int. Cl.
*F02D 41/14* (2006.01)
*G01N 25/62* (2006.01)
*F02D 41/26* (2006.01)

(52) U.S. Cl.
CPC ....... *F02M 35/10268* (2013.01); *G01N 25/62* (2013.01); *G01N 33/0016* (2013.01); *F02D 2200/0414* (2013.01); *F02D 2200/0418* (2013.01)

(58) Field of Classification Search
CPC ......... F02D 41/1494; F02D 2200/0418; F02D 2200/0414
See application file for complete search history.

(56) References Cited

U.S. PATENT DOCUMENTS

| | | | |
|---|---|---|---|
| 2005/0072212 A1* | 4/2005 | Oishi | G01N 27/16 73/23.21 |
| 2006/0134480 A1* | 6/2006 | Beasley | H01M 8/04037 429/413 |
| 2006/0237551 A1* | 10/2006 | Engler | G01N 27/223 236/44 C |
| 2012/0079879 A1 | 4/2012 | Saito et al. | |
| 2012/0253691 A1* | 10/2012 | Graf | G01N 27/223 702/24 |
| 2013/0062228 A1* | 3/2013 | Danilov | G02B 27/0006 206/216 |

FOREIGN PATENT DOCUMENTS

| | | |
|---|---|---|
| JP | 11-82746 A | 7/1989 |
| JP | 6-94658 | 4/1994 |
| JP | 2001-281182 A | 10/2001 |
| JP | 2013-216188 A | 10/2013 |

OTHER PUBLICATIONS

Japanese-language Written Opinion (PCT/ISA/210) issued in PCT Application No. PCT/JP2015/059022 dated Jun. 30, 2015 (Six (6) pages).
Extended European search report issued in counterpart European Patent Application No. 15774469.9 dated Sep. 11, 2017 (Seven (7) pages).
Chinese-language Office Action issued in Chinese Application No. 201580018210.6 dated Jul. 16, 2020 with English translation (19 pages).
Communication Pursuant to Article 94 (3) EPC issued in counterpart European Application No. EP 15774469.9 dated Jan. 21, 2021 (Five (5) pages).

* cited by examiner

HUMIDITY DETECTION DEVICE

TECHNICAL FIELD

The present invention relates to a humidity detector attached to an intake system of an internal combustion engine of an automobile.

BACKGROUND ART

Conventionally, automobiles using electronic control fuel injection systems have been widely used. In engine compartments of such automobiles, various sensors and control devices are disposed. As one of them, there is a humidity detector. Although humidity detectors have recently come into use for the purpose of fuel control, humidity detectors have conventionally been used mainly for air conditioning management in automobile cabins. When humidity detectors are used in automobile cabins, there is no requirement for durability or the like which presupposes a severe environment. For example, when a humidity detector is used integrally with the intake air flow measuring device or other sensors for the purpose of controlling an engine, the humidity detector is required to have environment-resistant performance equivalent to that of the intake air flow measuring device.

An environment particularly unfavorable to the humidity detector is adhesion of water droplets to a humidity detecting unit which originates from dew condensation of a detecting element unit, or the like. When moisture in air reaches a saturation point (relative humidity 100%), dew condensation occurs. A temperature at which dew condensation occurs is called a dew point. When dew condensation occurs on a humidity sensor, a significant delay is generated in detection responsiveness to changes in humidity and humidity measurement accuracy itself is negatively affected. In addition, there may be a case where the humidity detector loses a function thereof. When dew condensation occurs on the humidity detecting unit, a signal value indicating maximum or minimum humidity is output, and the humidity detector temporarily loses the function as a humidity detector until the detecting element unit dries. As a result, an engine control system is negatively affected while the function of the humidity detector is lost. This is a salient problem particularly when a polymer capacitance humidity sensor is used in an environment where an atmosphere rapidly changes such as inside of a vehicle intake pipe. A clear technical object is necessary to deal with the above problems.

PTL 1 is an example of a humidity detector including a countermeasure against dew condensation described above. PTL 1 discloses that dew condensation on a humidity detecting unit is prevented by obtaining a dew point temperature, and then heating, by a heating unit included therein, the humidity detecting unit to a temperature at which there is a certain difference between a sensor temperature and the dew point temperature.

CITATION LIST

Patent Literature

PTL 1: JP 2001-281182 A

SUMMARY OF INVENTION

Technical Problem

Since a formula for obtaining a dew point temperature is a polynomial, a processing load of a microprocessor increases when a dew point temperature is calculated each time. An intake system of an internal combustion engine of an automobile is affected by heat from the internal combustion engine, thereby being exposed to high temperatures. Therefore, reduction in a processing load of a microprocessor of a humidity detector is required. In addition, processes performed by the microprocessor tend to increase with improvement in performance and multifunctionality thereof, and reduction in a processing load for controlling prevention of dew condensation in the microprocessor is desired. PTL 1 leaves room for consideration of the above problems.

An object of the present invention is to provide a highly reliable humidity detector which reduces a processing load for preventing dew condensation.

Solution to Problem

In order to attain the object, the humidity detector of the present invention includes a humidity sensor provided with a humidity detecting unit and a temperature detecting unit, a heat generator which heats the humidity detecting unit, and a heating temperature control unit which controls a heating temperature of the heat generator. The humidity detector includes a target temperature storing unit which stores a plurality of target temperatures of the heat generator predetermined in accordance with temperature and humidity each of which is information detected by the humidity sensor.

Advantageous Effects of Invention

According to the present invention, it is possible to provide a highly reliable humidity detector which reduces a processing load for preventing dew condensation.

DESCRIPTION OF EMBODIMENTS

Hereinbelow, embodiments of the present invention will be described based on the drawings.

A first embodiment of the present invention will be described by using FIGS. 1 to 5.

Figure 1:
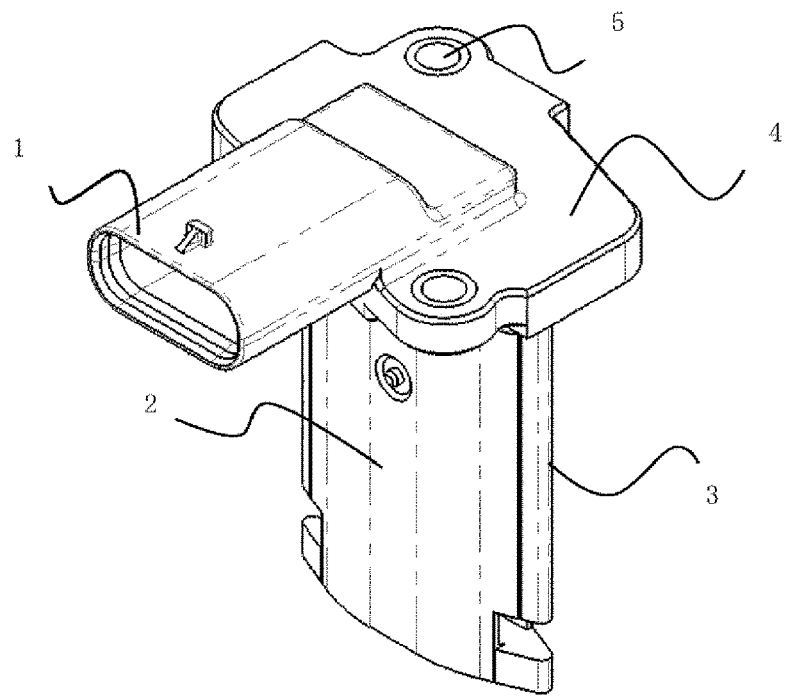
FIG. 1 is a perspective view of a humidity sensor according to an embodiment of the present invention.
Figure 2:
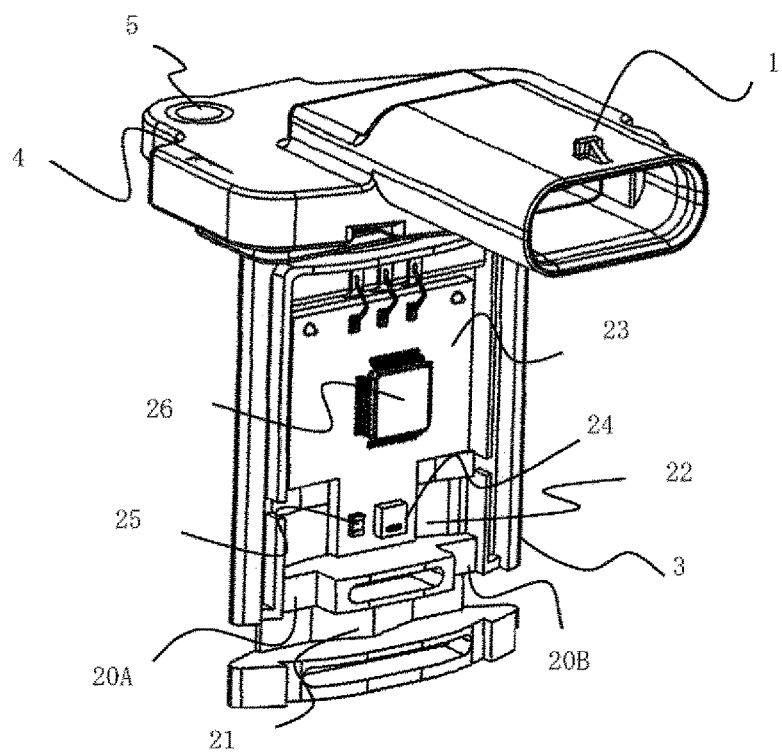
FIG. 2 is a configuration view of the humidity sensor according to the embodiment of the present invention.

As illustrated in FIGS. 1 and 2, a humidity detector attached to an intake pipe or a dedicated body (not illustrated) includes a housing 3, a cover 2, and an electronic circuit board 23 mounted on the housing 3. A microprocessor 26, a humidity sensor 24, and a heating resistor 24 are mounted on the circuit board 23.

The housing 3 includes a connector 1, a housing support 4, and a metal bush 5. The connector 1 is used for fitting to a harness of an engine control apparatus. The housing support 4 is fixed to the intake pipe or the dedicated body. The metal bush 5 is used for reinforcement when the intake pipe or the dedicated body and the housing support 4 are fixed with a metal screw or the like.

The housing 3 includes a subpassage constituting groove. The subpassage constituting groove constitutes a subpassage which takes in a part of air flowing in the intake pipe. The housing 3 constitutes the subpassage by the cooperation with the cover 2. The subpassage includes a first subpassage 21 which takes in a part of air flowing in the intake pipe, an inflow passage 20A to a second subpassage 22 from the first subpassage, and an inflow passage 20B to the first subpassage 21 from the second subpassage 22. The humidity sensor 24 and the heating resistor 25 are disposed in the second subpassage 22, and humidity of air flowing in the intake pipe is detected by the humidity sensor 24. The humidity sensor 24 is disposed in the second subpassage 22 provided so as to bypass the first subpassage 21, in other words, provided so as to diverge from the first subpassage 21, and thereby a configuration is obtained in which a pollutant hardly enters the second subpassage. Therefore, it is possible to prevent a pollutant from being carried to the humidity sensor.

Figure 3:
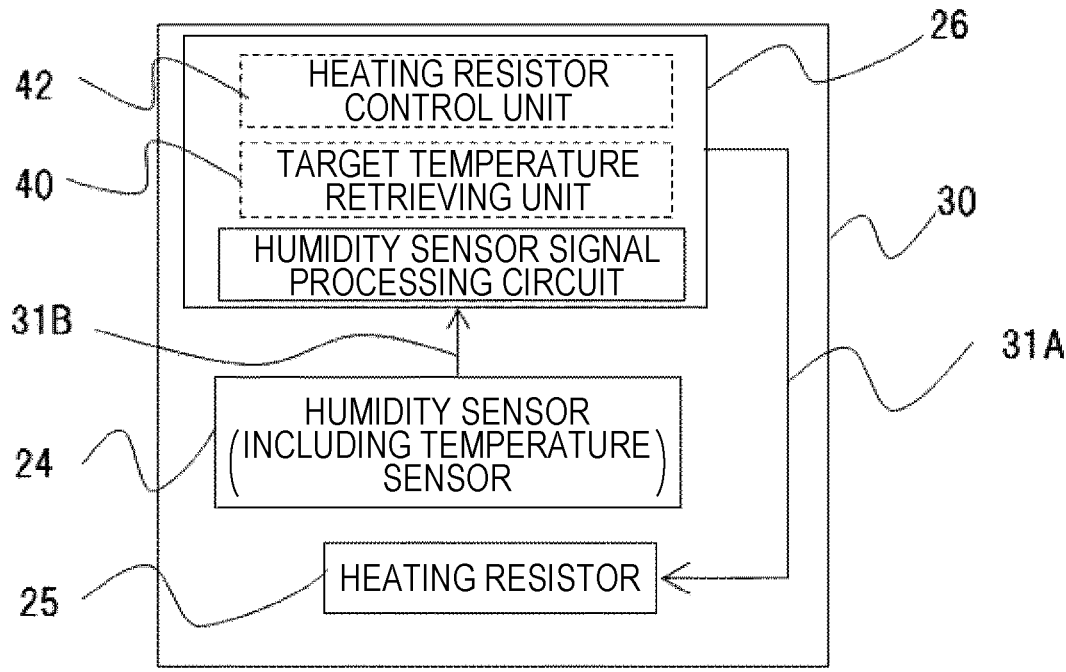
FIG. 3 is a block diagram of a heating control device of the humidity sensor according to the embodiment of the present invention.

Next, a countermeasure against dew condensation on the humidity sensor 24 will be described by using FIGS. 3 to 5. FIG. 3 is a block diagram of a heating temperature control device 30 of the heating resistor 26 which heats the humidity sensor 24.

As illustrated in FIG. 3, the heating temperature control device 30 includes the humidity sensor 24, the microprocessor 26, and the heating resistor 25. The humidity sensor 24 has a temperature detecting function in addition to a humidity detecting function, and temperature information and humidity information detected by the humidity sensor 24 are transmitted to the microprocessor 26 by using a signal line 31B for controlling the humidity sensor. The microprocessor 26 includes a humidity sensor signal processing circuit 43, a target temperature retrieving unit 40, and a heating element control unit 26. The humidity sensor signal processing circuit 43 processes a detection signal from the humidity sensor 24. The target temperature retrieving unit 40 retrieves a target temperature TT from the detection signal from the humidity sensor 24. The heating element control unit 26 controls a heating temperature of the heating resistor 25 based on the target temperature TT retrieved by the target temperature retrieving unit 40. The heating resistor control unit controls a heating temperature of the heating resistor to be the retrieved target temperature TT. Here, the heating temperature of the heating resistor is controlled by controlling a voltage supplied from a power supply unit not illustrated by ON/OFF control of a switching circuit not illustrated. The power supply unit and the switching circuit may be configured separately from the microprocessor 26, or may be configured integrally therewith. The microprocessor 26 controls the heating resistor by using a signal line 31A for controlling the heating resistor based on the temperature information and the humidity information.

Figure 4:
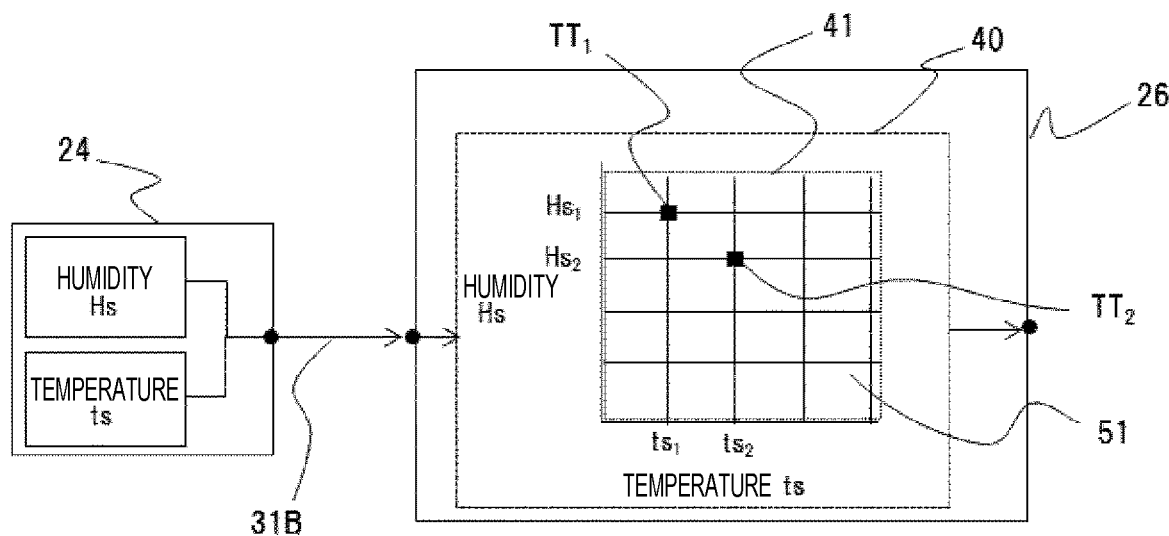
FIG. 4 is a block diagram of a unit for retrieving a heating target temperature value of a heating resistor, which according to the embodiment of the present invention.
Figure 5:
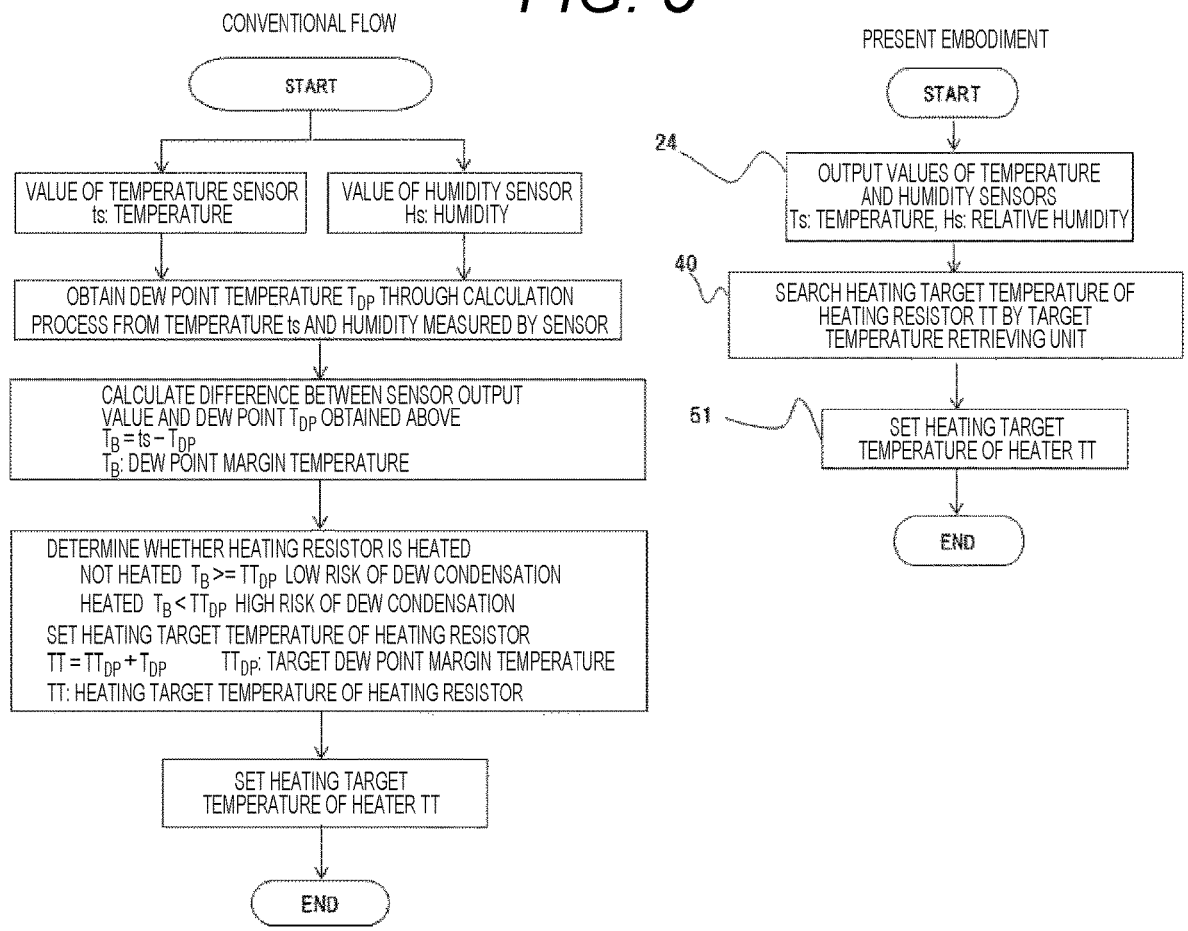
FIG. 5 is a flowchart of the heating control device of the humidity sensor according to the embodiment of the present invention.

As illustrated in FIG. 4, the target temperature TT corresponding to temperature ts and humidity Hs is stored as map data in a target temperature storing unit 41 of the microprocessor 26. In other words, the humidity detector includes a memory which stores the target temperature TT as map data. Measurement conditions, in other words, the temperature ts and the humidity Hs detected by the humidity sensor 24, which are retrieving conditions, are transmitted to the microprocessor 26 by using the signal line 31B for controlling the humidity sensor, and the target temperature retrieving unit retrieves a target temperature corresponding to the retrieving conditions from the map data. Here, the target temperature TT is a value calculated in advance.

A calculation example of the target temperature TT is as follows.

A calculation formula of relative humidity is represented by formula 1, where e denotes saturation vapor pressure [Pa] at a dew point temperature, es denotes saturation vapor pressure [Pa], ln denotes natural logarithm (logarithm to the base natural exponent e, loge x), and T denotes the absolute temperature [k]=(t° C.+273.15).

$$U[RH\%]=e/es\times 100 \quad \text{(formula 1)}$$

A calculation formula for obtaining saturation vapor pressure for water (ew) is represented by formula 2.

$$\ln(ew)[Pa]=-6096.9385\times T^{-1}+21.2409642-2.711193\times 10^{-2}\times T+1.67952\times 10^{-5}\times T^2+2.433502\times \ln(T) \quad \text{(formula 2)}$$

A calculation formula for calculating a dew point temperature from saturation vapor pressure is as follows.

$$y=\ln(e/611.213) \quad \text{(formula 3)}$$

When $y \geq 0$, $$TDP[°\ C.]=13.715\times y+8.4262\times 10-1\times y^2+1.9048\times 10^{-2}\times y^3+7.8158\times 10^{-3}\times y^4 \quad \text{(formula 4)}$$

When $y<0$, $$TDP[°\ C.]=13.7204\times y+7.36631\times 10^{-1}\times y^2+3.32136\times 10^{-2}\times y^3+7.78591\times 10^{-4}\times y^4 \quad \text{(formula 5)}$$

A flow for obtaining a heating target temperature value of a heating resistor TT is indicated as follows.

As an example of a flow of calculation for obtaining a dew point temperature $T_{DP}$ [° C.], measured temperature and measured humidity, which have been measured by the humidity sensor, are denoted by ts [° C.] and Hs [rh %], respectively.

Saturation vapor pressure es is obtained from measured temperature ts.

Formula 2 gives:

$$es=\text{EXP}^{\wedge}(-6096.9385\times(ts+273.15)^{-1}+21.2409642-2.711193\times 10^{-2}\times(ts+273.15)+1.673952\times 10^{-5}\times(ts+273.15)^2+2.433502\times \ln(ts+273.15)) \quad \text{(formula 6)}$$

Measured humidity Hs=U, accordingly, formulas 1 and 6 give:

$$e=U/100\times es=Hs/100\times \text{EXP}^{\wedge}(-6096.9385\times(ts+273.15)^{-1}+21.2409642-2.711193\times 10^{-2}\times(ts+273.15)+1.673952\times 10^{-5}\times(ts+273.15)^2+2.433502\times \ln(ts+273.15)) \quad \text{(formula 7)}$$

Formula 3 gives:

$$y=\ln(e/611.213)=\ln(Hs/100\times \text{EXP}^{\wedge}(-6096.9385\times(ts+273.15)^{-1}+21.2409642-2.711193\times 10^{-2}\times(ts+273.15)+1.673952\times 10^{-5}\times(ts+273.15)^2+2.433502\times \ln(ts+273.15))/611.23) \quad \text{(formula 8)}$$

Depending on a y value obtained from formula 8, the y value is substituted into
formula 4 when $y \geq 0$, or
formula 5 when $y<0$,
and thereby the dew point temperature $T_{DP}$[° C.] is calculated.

A calculation to obtain the target temperature TT [° C.] is as follows. First, a margin temperature $TT_{DP}$[° C.] to the dew point temperature is set in advance. Determination is performed in the following manner.

When ts$-T_{DP} \geq TT_{DP}$, the heating resistor is not controlled, and when ts$-T_{DP} < TT_{DP}$ the heating resistor is controlled.

The heating target temperature value of the heating resistor is derived from the measured values of temperature ts and humidity Hs measured by the humidity sensor 24 illustrated in FIG. 4, by calculating $TT = TT_{DP} + T_{DP}$.

In the first embodiment of the present invention, the microprocessor 26 is configured to store in advance, in the target temperature storing unit 41, the heating target temperature value of a heating resistor TT obtained by the above calculation formula for each temperature and each humidity, as map data, and to retrieve, by the target temperature retrieving unit 40, a target temperature in a measurement condition from the stored target temperature values.

Conventionally, a microprocessor has been caused to perform the calculation process for a countermeasure against dew condensation for each time, with the result that there has been a problem of an increase in a processing load of the microprocessor. In the embodiment, however, a configuration is adopted in which a process for obtaining a dew point temperature is not performed by the microprocessor 26, and the heating target temperature of a heating resistor TT stored in advance is retrieved based on the measurement condition. Consequently, it is possible to reduce the processing load of the microprocessor 26.

In addition, in the first embodiment of the present invention, a temperature sensor 27 included in the humidity sensor 24 measures a temperature of an atmosphere to be measured for retrieving the target temperature. In other words, a configuration is adopted in which the humidity sensor 24 including a temperature detecting unit measures a temperature of an atmosphere to be measured for retrieving the target temperature. According to the first embodiment of the present invention, since the humidity sensor 24 which measures humidity of an atmosphere to be measured also detects a temperature of the atmosphere to be measured, the temperature of the atmosphere to be measured in the vicinity of the humidity sensor 24 which needs to avoid new condensation can be measured with good accuracy and good responsiveness.

Particularly in a case of a humidity measuring device which detects humidity of intake air in an internal combustion engine of an automobile, it is necessary to perform humidity detection and control to prevent dew condensation at the same time under the circumstances where an intake air condition changes every moment. According to the first embodiment of the present invention, since the condition of the atmosphere to be measured in the vicinity of the humidity sensor 24 can be measured with good accuracy and good responsiveness, it is possible to perform humidity detection and control to prevent dew condensation at the same time even in the case described above.

In order to obtain a dew point temperature for each time as in conventional cases, it is necessary to measure a precise temperature of air before heating the humidity detecting unit. Therefore, separately from the temperature sensor provided at the humidity detecting unit, a dedicated air temperature sensor needs to be provided at a place which suffers less influence of heating of the humidity detecting unit. In other words, the air temperature sensor has to be disposed in a sensor housing. As a result, the size of the sensor housing increases to cause an increase in pressure loss in the intake pipe, limitation for circuit spaces, or the like, and thereby deterioration of performance and an increase in cost may be caused. According to the embodiment, deterioration of measurement accuracy resulting from dew condensation can be achieved by controlling the heating resistor with a temperature of the humidity sensor without using an additional temperature sensor, with lower cost than that in a case of a conventional humidity sensor used in the same environment.

Figure 6:
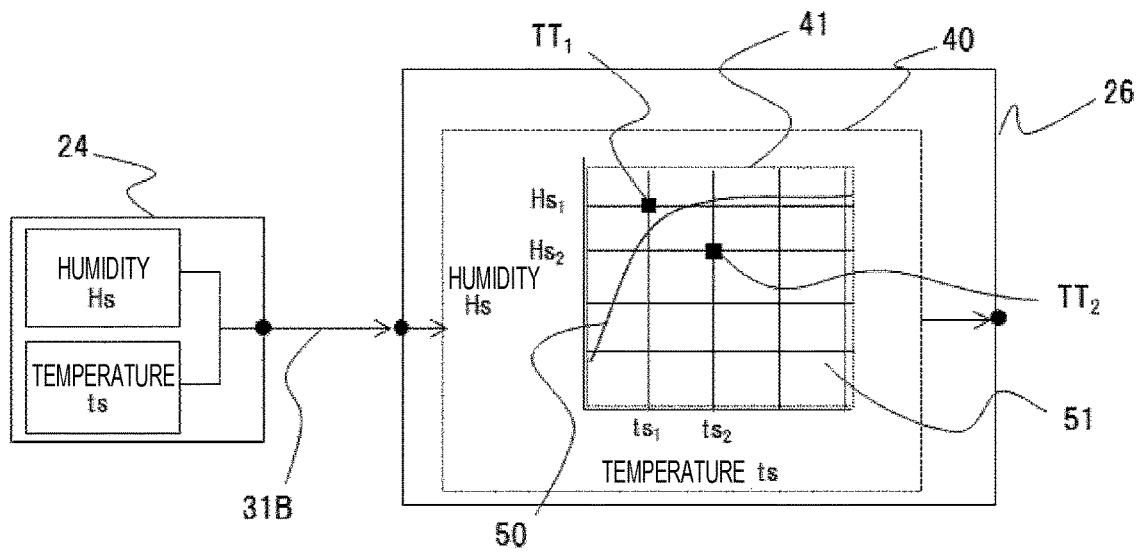
FIG. 6 is a block diagram illustrating a border line between energization and non-energization of a heating resistor according to an embodiment of the present invention.

A second embodiment of the present invention will be described by using FIG. 6. Regarding the same configuration as that in the first embodiment, a description thereof will be omitted.

The second embodiment of the present invention adopts a configuration in which a heating resistor is not controlled when a difference between a measured temperature ts and a dew point temperature $T_{DP}$ is greater than or equal to a margin temperature $TT_{DP}$, in other words, the measured temperature ts is higher than or equal to a target temperature TT. Specifically, when a measurement condition is a low temperature and high humidity condition (ts$_1$, Hs$_1$), target temperature $TT_1 \geq$ measured temperature ts$_1$ is satisfied, and the heating resistor is energized until the measured temperature ts$_1$ reaches a heating target temperature value $TT_1$ corresponding to the measurement condition. When the temperature increases and the humidity decreases by the heating control, the measurement condition exceeds a heating resistor heating border line 50 to be changed into, for example, a measurement condition (ts$_2$, Hs$_2$) and target temperature $TT_2 \leq$ measured temperature ts$_2$ is satisfied. In that case, the heating resistor is not energized and control thereof is not performed. Here, the target temperature TT which exceeds the heating resistance heating border line 50 is set to a temperature lower than or equal to a heat resistant temperature of an object to be heated.

Dew condensation can be prevented by heating the humidity detecting unit to a temperature higher than a dew point temperature. However, just simple energization of the resistor leads to further heating of the humidity detecting unit in a case of a high temperature environment, which may result in heating of the object to be heated to a temperature higher than or equal to a heat resistant temperature thereof, overheating thereof, and an extremely low humidity condition caused by high temperature. Consequently, there occurs a problem of deterioration of the measurement accuracy. According to the second embodiment of the present invention, the heating temperature of the heating resistor is controlled to be lower than the heat resistant temperature of the object to be heated, and therefore, it is possible to avoid overheating and the extremely low humidity condition to suppress the deterioration of the measurement accuracy.

Figure 7:
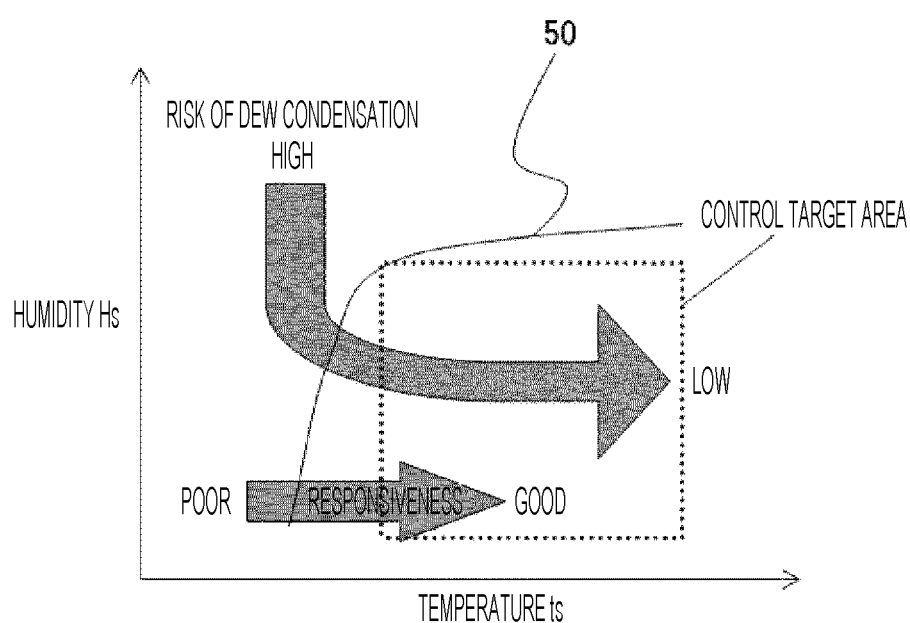
FIG. 7 is a block diagram illustrating a control target area of temperature and humidity according to an embodiment of the present invention.

A third embodiment of the present invention will be described by using FIG. 7. Regarding the same configuration as that in the first embodiment, a description thereof will be omitted.

In the third embodiment of the present invention, a margin temperature $TT_{DP}$ is set to a large value and a heating amount is increased in a low temperature and high humidity area where there is a high risk of dew condensation, and thereby the risk of dew condensation is decreased. On the other hand, in an area where there is a low risk of dew condensation, the margin temperature $TT_{DP}$, is set to a small value, thereby decreasing power consumption.

A fourth embodiment of the present invention will be described by using FIG. 7. Regarding the same configuration as that in the first embodiment, a description thereof will be omitted.

In addition to the above description, by setting a heating target temperature to a value obtained from a mixing ratio and target relative humidity, it is possible to predict a temperature and relative humidity to be reached, and to shift the temperature and the relative humidity into a temperature and humidity area existing specific to the humidity sensor where good accuracy and good responsiveness are exhibited. Consequently, the same result as that of conventional methods can be obtained at low cost.

REFERENCE SIGNS LIST 1 connector
2 cover
3 housing
4 housing support
5 metal bush
20A inflow passage
20B inflow passage
21 first subpassage
22 second subpassage
23 electronic circuit board
24 humidity sensor
25 heating resistor
26 microprocessor
27 temperature sensor
30 heating control device
31A signal line
31B signal line
40 target temperature retrieving unit
41 target temperature storing unit
42 heating resistor control unit.
43 temperature sensor signal processing circuit
50 border line between energization and non-energization of heating resistor
51 target temperature data
$TT_{DP}$ margin temperature
$T_{DP}$ dew point temperature
TT target temperature
ts measured temperature
Hs measured humidity
$TT_1$ target temperature
$ts_1$ measured temperature
$Hs_1$ measured humidity
$TT_2$ target temperature
$ts_2$ measured temperature
$Hs_2$ measured humidity

The invention claimed is:

1. A humidity detector comprising:
 a humidity sensor provided with a humidity detecting unit and a temperature detecting unit;
 a heat generator that heats the humidity detecting unit;
 a microprocessor including
  a heating temperature control unit that controls a heating temperature of the heat generator, and
  a target temperature storing unit that stores a plurality of calculated target temperatures of the heat generator, the plurality of calculated target temperatures of the heat generator being stored for each temperature and each humidity.

2. The humidity detector according to claim 1, comprising a retrieving unit that retrieves, from the target temperature storing unit, a target temperature corresponding to temperature and humidity information detected by the humidity sensor, wherein
 the heating temperature control unit controls a heating temperature of a heating resistor to achieve the retrieved target temperature.

3. The humidity detector according to claim 2, wherein the target temperature is set to be higher than a dew point temperature obtained from humidity and a temperature used in retrieval by at least a predetermined value.

4. The humidity detector according to claim 2, wherein the heating resistor is energized when a detected temperature is lower than the target temperature, and the heating resistor is not energized when the detected temperature is higher than the target temperature.

5. The humidity detector according to claim 3, wherein the target temperature is lower than or equal to a heat resistant temperature of an object to be heated.

6. The humidity detector according to claim 3, wherein the lower the dew point temperature, the larger the predetermined value is set.

7. The humidity detector according to claim 2, wherein the microprocessor includes the retrieving unit.

8. The humidity detector according to claim 1, further comprising a housing that contains the humidity sensor, the heat generator, and the microprocessor on a circuit board therein.

9. The humidity detector according to claim 8, wherein the humidity sensor, the heat generator, and the microprocessor are all immediately adjacent to the circuit board.

10. The humidity detector according to claim 9, wherein the target temperature storing unit stores the plurality of calculated target temperatures in advance as map data.

11. The humidity detector according to claim 1, wherein the plurality of calculated target temperatures are calculated using an equation that includes terms associated with a saturation vapor pressure, a dew point temperature, and an absolute temperature.

* * * * *